United States Patent [19]

Forster et al.

[11] 4,087,463

[45] May 2, 1978

[54] HYDROGENOLYSIS OF HYDROBENZOINS

[75] Inventors: Denis Forster; George F. Schaefer, both of St. Louis, Mo.

[73] Assignee: Monsanto Company, St. Louis, Mo.

[21] Appl. No.: 753,042

[22] Filed: Dec. 22, 1976

[51] Int. Cl.$^2$ .................. C07C 41/00; C07C 1/22
[52] U.S. Cl. ..................... 260/613 A; 260/600 R;
  260/668 R; 260/613 R; 260/515 R; 260/515 P;
  260/465 R; 260/465 H; 260/612 R; 260/649 R;
  560/57; 568/729; 568/723
[58] Field of Search ............ 260/613 A, 619 B, 667,
  260/668 R, 668 C, 613 R, 619 R, 515 R, 515 P,
  465 R, 465 H, 612 R, 479 R, 476 R, 649 R

[56] References Cited

FOREIGN PATENT DOCUMENTS 877,882  9/1961  United Kingdom.

OTHER PUBLICATIONS

Wender et al., J.A.C.S., vol. 73 (1951) 2656–2658.

*Primary Examiner*—Bernard Helfin
*Attorney, Agent, or Firm*—Wendell W. Brooks; Joseph D. Kennedy; James W. Williams

[57] ABSTRACT

Hydrogenolysis of hydrobenzoins [1,2-bis(aryl)ethane-1,2-diols] in the presence of a catalyst comprising cobalt carbonyl yields 1,2-bis(aryl)ethanes. The process is particularly directed to the production of 1,2-bis(4-hydroxyphenyl)ethane from 4,4-dihydroxyhydrobenzoin [1,2-bis(4-hydroxyphenyl)ethane-1,2-diol].

30 Claims, No Drawings

HYDROGENOLYSIS OF HYDROBENZOINS

BACKGROUND OF THE INVENTION

This invention relates to the hydrogenolysis of hydrobenzoins [1,2-bis(aryl)ethane-1,2-diols]. It represents an efficient and highly selective way of removing the 1,2-diol functionality from hydrobenzoins. More particularly, this invention relates to the hydrogenolysis of hydrobenzoins in the presence of a catalyst comprising cobalt carbonyl to yield 1,2-bis(aryl)ethanes in which the hydrobenzoin 1,2-diol functionality has been removed efficiently and selectively.

Hydrogenolysis of benzylic alcohols to hydrocarbons under mild conditions with heterogeneous catalysts, particularly palladium on charcoal, is well known in the art. See, for example, Baltzly et al, *JOURNAL OF THE AMERICAN CHEMICAL SOCIETY* 65, 1984 (1943). Thus benzyl alcohol is readily amenable to hydrogenolysis by most common hydrogenolysis catalysts. However, when such commonly employed catalysts are routinely applied to hydrobenzoins, they suffer from several disadvantages, the most obvious of which is their failure in many instances to induce the desired hydrogenolysis. For example, 4,4'-dihydroxyhydrobenzoin fails to react when subjected to hydrogenolysis under conditions similar to those employed by Baltzly et al. Similarly, although good selectivity for the hydrogenolysis of hydrobenzoin to 1,2-diphenylethane (bibenzyl) using platinum on carbon (charcoal) and alcoholic palladium chloride as the catalyst has been described in Zelinsky et al, *Chemische Berichte*, 66, 872 (1933), the extension of the catalyst to other hydrobenzoins, for example, 4,4'-dihydroxyhydrobenzoin is nevertheless unsuccessful.

Furthermore, such commonly employed hydrogenolysis catalysts are not easily recycled for reuse in subsequent hydrogenolysis reactions. As a result, the routine use of such catalysts for large technical scale processes is prohibitively wasteful and expensive.

Hydrogenolysis of benzylic alcohols to hydrocarbons with homogeneous catalysts, for example, dicobalt octacarbonyl and/or cobalt hydrocarbonyl has also been described. See, for example, Wender et al, *Journal of the American Chemical Society*, 73, 2656 (1951). The selectivity for production of toluene from benzyl alcohol, however, was reported to be only 63 percent, with 32 percent selectivity for the homologation product, 2-phenylethanol.

It is therefore an object of the present invention to overcome the above disadvantages and therefore provide an improved and more economically and commercially feasible hydrogenolysis process in which a mixture of hydrogen and carbon monoxide is employed with a homogeneous catalyst comprising cobalt carbonyl to hydrogenolyze hydrobenzoins to form 1,2-bis(aryl)ethanes.

Another object of the present invention is to provide a more selective and reactive hydrogenolysis system for the removal of the 1,2-diol functionality from hydrobenzoins, while simultaneously facilitating product isolation and catalyst recovery and recycle for reuse in subsequent reactions without substantial catalyst decomposition and loss.

Still another object of the present invention is to provide a hydrogenolysis process enabling the efficient and selective production of 1,2-bis(4-hydroxyphenyl)ethane from 4,4'-dihyroxyhydrobenzoin.

These and other objects will become apparent to those skilled in the art from the accompanying description of the invention.

SUMMARY OF THE INVENTION

According to the present invention, it has been discovered that hydrobenzoins [1,2-bis(aryl)ethane-1,2-diols] can be effectively and efficiently hydrogenolyzed to the corresponding 1,2-bis(aryl)ethanes by contacting the hydrobenzoin in an inert solvent system at hydrogenolysis conditions with a gaseous mixture of hydrogen and carbon monoxide and a catalyst comprising cobalt carbonyl for a time sufficient to cause hydrogenolysis of the hydrobenzoin 1,2-diol functionality carbon-oxygen bonds. The oxygen so cleaved from each carbon atom of the 1,2-diol functionality during the hydrogenolysis is replaced by a hydrogen atom.

The 1,2-bis(aryl)ethane products obtained in the present process can be recovered by any of a number of well-known and conventional procedures. Thus the hydrogenolysis of hydrobenzoins according to the present invention provides an efficient and effective process for the conversion of hydrobenzoins to 1,2-bis(aryl)ethanes—in general with a greater than 70 percent selectivity, although this might vary with the particular hydrobenzoin in question. Simultaneously, catalyst recovery and recycle for reuse in subsequent reactions is facilitated without substantial decomposition and loss.

DETAILED DESCRIPTION OF THE INVENTION

Hydrogenolysis of hydrobenzoins in the presence of a catalyst comprising cobalt carbonyl yields 1,2-bis(aryl)ethanes. The process is characterized by having the catalyst completely soluble (dissolved) in the inert solvent system, although the particular substrate (a hydrobenzoin) need only be partially soluble. That is, the hydrobenzoin need only be soluble to the extent necessary to permit the hydrogenolysis to proceed at a reasonable rate.

The term "cobalt carbonyl" as used herein refers to any compound containing cobalt and one or more carbonyl ligands. Non-limiting examples of this are dicobalt octacarbonyl, $Co_2(Co)_8$, and cobalt hydrocarbonyl, $HCo(CO)_4$.

In accordance with the present process, the hydrobenzoin is contacted in an inert solvent system at hydrogenolysis conditions with a gaseous mixture of hydrogen and carbon monoxide and a catalyst comprising cobalt carbonyl for a time sufficient to cause hydrogenolysis of the 1,2-diol functionality carbon-oxygen bonds.

As referred to hereinabove, the catalyst essential for use in the present invention comprises cobalt carbonyl. Specifically, the active component of the catalyst in the process of the present invention is believed to be dicobalt octacarbonyl, $Co_2(CO)_8$, and/or cobalt hydrocarbonyl (cobalt tetracarbonyl hydride), $HCo(CO)_4$; however, the direct charging of either of these species is not required. The charging of any cobalt(II) compound which can be converted in situ into dicobalt octacarbonyl and/or cobalt hydrocarbonyl under the reaction conditions employed and which causes no adverse side effects is sufficient. Among the cobalt(II) compounds which may be charged to the reaction vessel, for example, an autoclave, to provide what is believed to be the active form or component of the catalyst of the present invention are cobalt(II) salts, cobalt(II) oxide, and the like. Specific example of cobalt(II) compounds capable of providing the active catalyst of the present invention may be taken from the following nonlimiting partial list of suitable cobalt(II) compounds, which partial list includes dicobalt octacarbonyl, cobalt hydrocarbonyl, cobalt(II) acetate, cobalt(II) formate, cobalt(II) propionate, cobalt(II) butanoate, cobalt(II) benzoate, cobalt(II) citrate, cobalt(II) oxalate, cobalt(II) tartrate, cobalt(II) carbonate, cobalt(II) bromide, cobalt(II) chloride, cobalt(II) iodide, cobalt(II) nitrate, cobalt(II) phosphate, cobalt(II) sulfate, cobalt(II) hydroxide, cobalt(II) oxide, and various hydrates of the above-named compounds, and the like.

While not desiring to be bound by the theory of the present invention or to limit the present invention in any way, it is believed that when neither dicobalt octacarbonyl nor cobalt hydrocarbonyl is directly charged to the reaction vessel in which the hydrogenolysis is conducted, the cobalt(II) compound so charged undergoes reduction and carbonylation in situ under the reaction conditions employed to provide the active catalyst. Equation (1) shows the reaction involved, with cobalt(II) acetate being used for purposes of illustration.

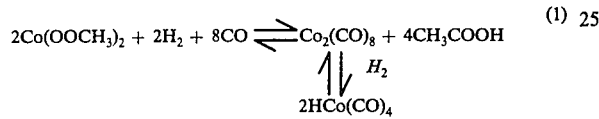

(1)

It will be noted, however, that catalysis is basically an inexact science, that is, an empirical art, unenlightened by rules decreeing certainty and predictability. It follows therefore that various other cobalt carbonyl species, in addition to dicobalt octacarbonyl and cobalt hydrocarbonyl, may also be produced under reaction conditions employed in the present process. Such other species, if present, may in fact be, in whole or in part, the actual active catalyst component or components. As noted hereinabove, however, all such species are conveniently referred to as "cobalt carbonyl."

Thus the present invention contemplates the hydrogenolysis of the present invention occurring in the presence of a catalyst comprising cobalt carbonyl, regardless of the source or the actual active component or species involved.

The process of the present invention is carried out in an acidic reaction medium, insofar as acidity and basicity is concerned. Attention is drawn to the fact that cobalt hydrocarbonyl is a strong acid with a dissociation constant comparable to that of nitric acid. And as noted hereinabove, cobalt hydrocarbonyl is believed to be one of the active catalytic components or species for the hydrogenolysis of the present process. As a result, the presence of basic type species or ligands which cause the destruction of cobalt hydrocarbonyl or which form species or products therewith which are catalytically inactive under process conditions for effecting the desired hydrogenolyses are to be avoided. For example, species such as ammonia, amines, including pyridine and the like, organo-phosphines, including tri-n-butylphosphine and the like are to be avoided as the desired hydrogenolyses fail to occur to any significant extent when one or more of these species are present in the reaction medium.

Solvents desirable for use in the present invention must be compatible with the present process. That is, the solvent (a) must be inert under reaction conditions; (b) must dissolve the cobalt carbonyl catalyst; and (c) must be capable of dissolving sufficient amounts of the hydrobenzoin starting material to allow the desired hydrogenolysis to proceed at a reasonable rate. Additionally, it is desirable, albeit not required, that the product exhibit low solubility in the solvent. Solvents which in general meet these requirements are $C_2$ to $C_{10}$ aliphatic alcohols. Of these alcohols, those preferred are the $C_4$ to $C_6$ alcohols, with $C_4$ alcohols, for example, 1-butanol, being most preferred in that certain of the 1,2-bis(aryl)ethane final products, for example, 1,2-bis(4-hydroxyphenyl)ethane, exhibit desirably low solubility therein.

It will be noted that carboxylic acids are generally not suitable as solvents and are to be avoided in that the desired hydrogenolysis is in general severely retarded when carboxylic acids, for example, acetic acid, are employed as solvents. It is suggested that one rationale for the observed retardation is that by virtue of the equilibrium existing between the initially charged cobalt(II) compound and dicobalt octacarbonyl as illustrated in Equation (1), the presence of added carboxylic acid could tend to drive the reaction [Equation (1)] to the left, and thereby prevent to a substantial extent, the formation of the cobalt octacarbonyl. And, as noted hereinabove, dicobalt octacarbonyl is believed to be one of the active catalytic components or species involved along with cobalt hydrocarbonyl.

In contrast, water may be present in the reaction medium, at least in the sense that the inert solvent system need not be anhydrous. Water is also produced in the reaction. It is nevertheless preferred to avoid either the addition or the presence of greater than nominal amounts of water. That is, the reaction medium should contain no more than nominal amounts of water.

The hydrobenzoins suitable for use in the present process are represented by the formula:

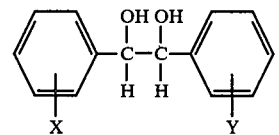

in which X and Y each independently represent hydrogen, alkyl of 1 to 8 carbon atoms, hydroxy, alkoxy containing an alkyl of 1 to 8 carbon atoms, acyloxy containing an alkyl of 1 to 8 carbon atoms or a phenyl, carboxy, cyano, halogen, and any other non-interfering substituent. Representative of such hydrobenzoins are hydrobenzoin, 2-methylhydrobenzoin, 2,2'-dimethylhydrozenzoin, 3-methylhydrobenzoin, 3,3'-dimethylhydrobenzoin, 4-methylhydrobenzoin, 4,4'-dimethylhydrobenzoin, 2-ethylhydrobenzoin, 2,2'-diethylhydrobenzoin, 3-ethylhydrobenzoin, 3,3'-diethylhydrobenzoin, 4-octylhydrobenzoin, 4,4'-dioctylhydrobenzoin, 2-hydroxyhydrobenzoin, 2,2'-dihydroxyhydrobenzoin, 3-hydroxyhydrobenzoin, 3,3'-dihydroxyhydrobenzoin, 4-hydroxyhydrobenzoin, 4,4'-dihydroxyhydrobenzoin, 2-methoxyhydrobenzoin, 2,2'-dimethoxyhydrobenzoin, 3-methoxyhydrobenzoin, 3,3'-dimethoxyhydrobenzoin, 4-methoxyhydrobenzoin, 4,4'-dimethoxyhydrobenzoin, 2-ethoxyhydrobenzoin, 2,2'-diethoxyhydrobenzoin, 3-ethoxyhydrobenzoin, 3,3'-diethoxyhydrobenzoin, 4-ethoxyhydrobenzoin, 4,4'-diethoxyhydrobenzoin, 2-octoxyhydrobenzoin, 2,2'-dioctoxyhydrobenzoin, 3-octoxyhydrobenzoin, 3,3'-dioctoxyhydrobenzoin, 4-octoxyhydrobenzoin, 4,4′-dioctoxyhydrobenzoin, 2-acetoxyhydrobenzoin, 2,2′-diacetoxyhydrobenzoin, 3-acetoxyhydrobenzoin, 3,3′-diacetoxyhydrobenzoin, 4-acetoxyhydrobenzoin, 4,4′-diacetoxyhydrobenzoin, 2-benzoxyhydrobenzoin, 2,2′-dibenzoxyhydrobenzoin, 3-benzoxyhydrobenzoin, 3,3′-dibenzoxyhydrobenzoin, 4-benzoxyhydrobenzoin, 4,4′-dibenzoxyhydrobenzoin, 2-carboxyhydrobenzoin, 2,2′-dicarboxyhydrobenzoin, 3-dicarboxyhyrobenzoin, 3,3′-dicarboxyhydrobenzoin, 4-carboxyhydrobenzoin, 4,4′-dicarboxyhydrobenzoin, 2-cyanohydrobenzoin, 2,2′-dicyanohydrobenzoin, 3-cyanohydrobenzoin, 3,3′-dicyanohydrobenzoin, 4-cyanohydrobenzoin, 4,4′-dicyanohydrobenzoin, 2-chlorohydrobenzoin, 2,2′-dichlorohydrobenzoin, 3-chlorohydrobenzoin, 3,3′-dichlorohydrobenzoin, 4-chlorohydrobenzoin, 4,4′-dichlorohydrobenzoin, 2-bromohydrobenzoin, 2,2′-dibromohydrobenzoin, 4-bromohydrobenzoin, 4,4′-dibromohydrobenzoin, 2-iodohydrobenzoin, 2,2′-diiodohydrobenzoin, 3-iodohydrobenzoin, 3,3′-diiodohydrobenzoin, 4-iodohydrobenzoin, 4,4′-diiodohydrobenzoin, 2-fluorohydrobenzoin, 2,2′-difluorohydrobenzoin, 3-fluorohydrobenzoin, 3,3′-difluorohydrobenzoin, 4-fluorohydrobenzoin, 4,4′-difluorohydrobenzoin, and the like.

Other compounds, capable of being converted in situ into the hydrobenzoins represented by the formula hereinabove under reaction conditions employed in the present process, are also suitable for use in the present process. Such compounds include precursor compounds, for example, the benzoins and benzyls corresponding to the hydrobenzoins listed hereinabove. Illustrative examples include 4-hydroxybenzoin, 4′-hydroxybenzoin, 4-hydroxybenzil (all of which can be converted to 4-hydroxyhydrobenzoin), 4-methoxybenzoin, 4′-methoxybenzoin, 4-methoxybenzil (all of which can be converted to 4-methoxyhydrobenzoin) 3-carboxybenzoin, 3′-carboxybenzoin, 3-carboxybenzil (all of which can be converted to 3-carboxyhydrobenzoin), 4,4′-dimethoxybenzoin (anisoin), 4,4′-dimethoxybenzil (both of which can be converted to 4,4′-dimethoxyhydrobenzoin), 4,4′-dihydroxybenzoin, 4,4′-dihydroxybenzil (both of which can be converted to 4,4′-dihydroxyhydrobenzoin), and the like.

Of the compounds suitable for use in the present process, 4,4′-dihydroxyhydrobenzoin (and compounds capable of being converted in situ thereto under reaction conditions) are particularly important in that the hydrogenolysis product therefrom, 1,2-bis(4-hydroxyphenyl)ethane (bisphenol E or simply PBE), is very useful as an intermediate in the preparation of epoxy resins, polycarbonates, polyesters, and other synthetic materials.

Similarly, other compounds among those suitable for use in the present process which contain functional groups capable of undergoing useful reactions for example, condensations and the like may also be important. Such compounds include, for example, 4,4′-dicarboxyhydrobenzoin, 4,4′-dicyanohydrobenzoin, and the like.

As indicated hereinabove, the hydrogenolysis of the present invention is carried out by contacting the hydrobenzoin in an inert solvent system at hydrogenolysis conditions with a gaseous mixture of hydrogen and carbon monoxide and a catalyst comprising cobalt carbonyl for a time sufficient, in general between 1 hour and about 5 hours, to form the hydrogenolysis product. The reaction of the present invention can in general be illustrated:

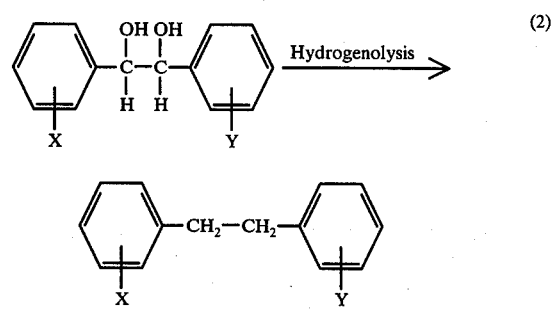
(2)

in which X and Y are as defined hereinabove. Equation (3) illustrates a specific embodiment of the present invention, the hydrogenolysis of 4,4′-dihydroxyhydrobenzoin to yield 1,2-bis(4-hydroxyphenyl)ethane, also known as bisphenol E or simply BPE.

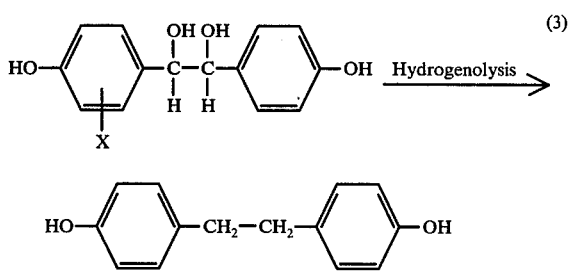
(3)

Gas chromatographic-mass spectral analysis of the final products and also of intermediate samples withdrawn from the reaction mixture during the hydrogenolysis shown in Equation (3) indicate that Compound I is formed as an intermediate in the reaction and that Compounds II, III, IV, V, and IV (where R is an alkyl group corresponding to that of the alcohol used as a solvent) are the principal by-products in the final reaction mixtures. These are shown in TABLE 1.

TABLE 1.

| INTERMEDIATES AND PRINCIPAL BY-PRODUCTS FROM THE HYDROGENOLYSIS OF 4,4′-DIHYDROXYHYDROBENZOIN | | |
|---|---|---|
| COMPOUND | STRUCTURE[a] | NAME |
| I | HO—⌬—C(=O)—CH₂—⌬—OH | 4,4′-Dihydroxybenzoin |
| II | (HO—⌬—)₂CHCH₂OH | 2,2-Bis(4-hydroxyphenyl)-ethanol |

TABLE 1.-continued
INTERMEDIATES AND PRINCIPAL BY-PRODUCTS FROM THE HYDROGENOLYSIS OF 4,4'-DIHYDROXYHYDROBENZOIN

| COMPOUND | STRUCTURE[a] | NAME |
|---|---|---|
| III | (HO—⟨⟩—)$_2$ CHCH$_2$OR | Alkoxy 2,2-bis(4-hydroxyphenyl)ethane |
| IV | (HO—⟨⟩—)$_2$ CHCOOR | Alkyl 2,2-bis(4-hydroxyphenyl)-acetate |
| V | HO—⟨⟩—CH(CH$_2$OH)—CH$_2$—⟨⟩—OH | 2,3-Bis(4-hydroxyphenyl)-1-propanol |
| VI | HO—⟨⟩—CH(CH$_2$OR)—CH$_2$—⟨⟩—OH | Alkoxy 2,3-bis(4-hydroxyphenyl)propane |

[a] R is an alkyl group corresponding to that of the alcohol used as a solvent, for example, n-butyl from 1-butanol.

From the results shown in TÅBLE 1, it is speculated that the overall reaction of 4,4'-dihydroxyhydrobenzoin (and by analogy, the reaction of other suitable hydrobenzoins) can be represented as being divided into two basic steps—(a) acid catalyzed carbonium ion rearrangement with either hydride or 4-hydroxyphenyl (in general, aryl) migration

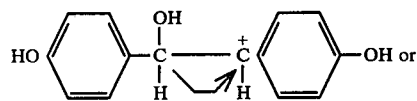

-continued

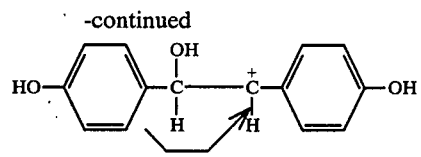

and (b) hydrogenation of the rearranged products.

Thus it is believed that the hydrogenolysis of 4,4'-dihydroxyhydrobenzoin to 1,2-bis(4-hydroxyphenyl)ethane (and, again, by analogy, the hydrogenolysis of other suitable hydrobenzoins to the corresponding hydrogenolysis products) occurs as shown in REACTION SCHEME 1, with cobalt hydrocarbonyl being indicated, for convenience, as the catalyst.

REACTION SCHEME 1

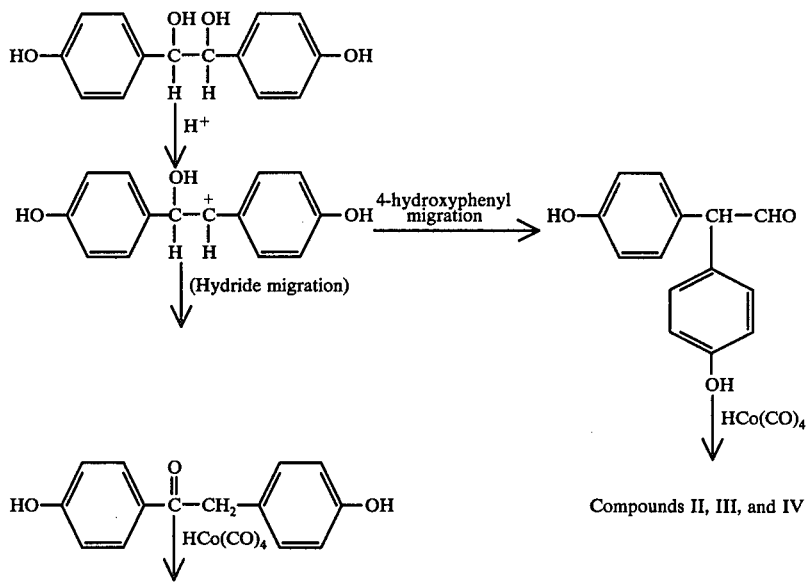

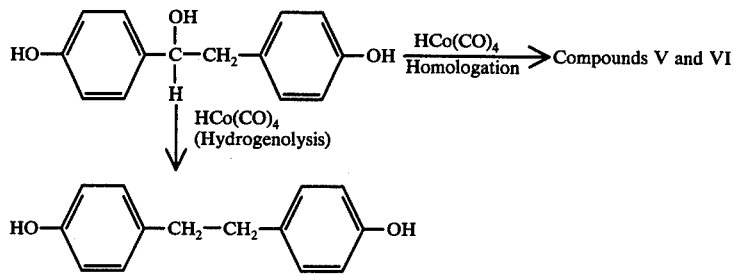

Attention is drawn to the fact, however, that whatever the actual mechanistic pathway, whether as shown in REACTION SCHEME 1 or some other equally plausible pathway, the present invention contemplates in general the hydrogenolysis of the hydrobenzoin to yield the corresponding 1,2-bis(aryl)ethane and in particular the hydrogenolysis of 4,4'-dihydroxyhydrobenzoin to yield 1,2-bis(4-hydroxyphenyl)ethane).

The concentration of the hydrobenzoins is not narrowly critical. While it is desirable to have all of the hydrobenzoin starting material dissolved or in solution, in practice it is necessary only to have sufficient amounts dissolved in order to permit the desired hydrogenolysis to proceed at a reasonable rate. In this regard, it will be noted that many of the hydrobenzoin starting compounds are only moderately soluble in the inert solvents of choice. However, as the desired reaction proceeds under the hydrogenolysis conditions employed in the present process, additional hydrobenzoin starting material dissolves, thereby maintaining a continuous supply of dissolved hydrobenzoin starting material available for reaction so long as some undissolved hydrobenzoin starting material remains. This phenomenon permits the desired hydrogenolysis to proceed to completion in an effective and efficient manner.

The concentration of the cobalt carbonyl (or the compounds capable of being converted thereto under reaction conditions) can vary widely from very low concentrations to very high concentrations. However, since the rate of the desired hydrogenolysis is (in part) dependent upon the concentration of the catalyst, preferred concentration will often be in the range of about 0.05 molar to about 0.5 molar. At concentrations within the preferred range, the desired hydrogenolysis proceeds to completion at a reasonable rate. On the other hand, although the reaction still occurs at lower concentrations, the rate is undesirably slow. Higher concentrations of course do not suffer from slow rates and may be employed, if desired—the only limits being practicality and cost as well as the fact that since the catalyst must be in solution, the amount utilized will be no greater than will dissolve in the inert solvent system.

The hydrogenolysis conditions utilized in the present process can vary within fairly wide limits. However, since the present process is temperature dependent, the temperature should be maintained between about 160° C and about 250° C, with the preferred temperature being between about 170° C and about 220° C, and usually about 200° C. It will be recognized, however, that the temperature actually employed will depend to some extent on the particular hydrobenzoin starting material. At the preferred temperatures the selectivity of the desired 1,2-bis(aryl)ethane product is in general greater than 70 percent. However, the selectivity becomes increasingly worse as the temperature is lowered, as indicated in TABLE 2, hereinbelow, for the hydrogenolysis of 4,4'-dihydroxyhydrobenzoin to 1,2-bis(4-hydroxyphenyl)ethane.

Thus, as the temperature is lowered, particularly below about 160° C, the hydrobenzoin tends to undergo a pinacol rearrangement involving an aryl migration, rather than the preferred hydride migration to produce undesired by-products to the increasing exclusion of the desired 1,2-bis(aryl)ethane.

The total initial pressure within the reaction vessel for the gaseous mixture of hydrogen and carbon monoxide will generally range between about 1500 pounds per square inch gauge (hereinafter, psig) and about 10,000 psig, with the upper limit being imposed more for practical reasons than for reasons to avoid any adverse effect upon the yield and selectivity of the desired product. The preferred initial pressure, however, is between about 2000 psig and 4000 psig.

At the pressure ranges described hereinabove, the partial pressure or molar ratio of hydrogen to carbon monoxide may vary between about 1:10 and about 5:1. However, the preferred molar ratio is within the range of about 1:6 to about 3:1. In any event, whatever the actual molar ratio employed, sufficient amounts of carbon monoxide must be present in order to maintain catalyst stability. Similarly, sufficient amounts of hydrogen are required in order to effect the desired hydrogenolysis.

The time required for the desired hydrogenolysis to occur is not critical. Generally, a reaction time between about 1 hour and about 5 hours is required for complete reaction, with about 1 hour usually being sufficient. It will of course be recognized, however, that the actual reaction time required will vary with the hydrobenzoin starting material and the temperature and pressure, and the like employed.

The present process is suited to either batch or continuous operations. Continuous operations can involve recirculation of the inert solvent system along with the catalyst comprising cobalt carbonyl following isolation of the hydrogenolysis product. Additional hydrobenzoin starting material can then be charged to the reaction vessel to continue the process in a subsequent reaction.

The 1,2-bis(aryl)ethane products obtained in the present process can be readily recovered by any of a number of well-known and conventional procedures. It will be understood, however, that the isolation procedures employed in the procedural examples and discussed hereinbelow are primarily for illustrative purposes. Other procedures can be employed, and may be preferred, for commercial use.

Upon completion of the reaction, the product solution is cooled to a desired temperature. For those products, for example, 1,2-bis(4-hydroxyphenyl)ethane, which exhibit low solubility in the inert solvents of choice at ambient and sub-ambient temperatures, the product solution can be cooled to ambient, or even lower, temperatures to induce crystallization of the product. The crystalline product may then be collected by suction filtration. Recrystallization from a suitable solvent, for example, ethanol, acetone, and the like yields the pure 1,2-bis(aryl)ethane, for example, 1,2-bis(4-hydroxyphenyl)ethane, product.

Alternatively, if the cooling process is interrupted above ambient temperatures, for example, 45° C to about 75° C, a homogeneous solution is obtained, even for those products which exhibit low solubility in the solvents of choice at ambient and sub-ambient temperatures. In such an event, particularly for those products which are highly soluble in the solvents of choice, the cobalt values may be recovered from the product solution by various recovery methods recited in the voluminous art pertaining to the so-called oxy synthesis and regenerated to form a viable catalyst comprising cobalt carbonyl. For example, methods described in Gwynn et al, U.S. Pat. No. 3,361,829; Cull et al, U.S. Pat. No. 3,118,949; Roming, Jr., U.S. Pat. No. 3,055,942; Johnson et al, U.S. Pat. No. 2,919,292; and Mertzweiller, U.S. Pat. No. 2,841,617 may be employed. Also, for a general review of procedures utilized in the oxy synthesis to recover cobalt values, see Gavrilova et al, *The Soviet Chemical Industry*, 6(10), 607–620 (1974), and references cited therein.

Once the cobalt values are recovered from the product solution, the product may be isolated and purified by conventional means, such as, for example, evaporation of the solvent in vacuo followed by recrystallization from a suitable solvent, for example, those noted hereinabove, to yield pure 1,2-bis(aryl)ethane.

It will be noted that while utilization of the former isolation procedure, when appropriate, may result in somewhat lower initial yield of 1,2-bis(aryl)ethane product in that a portion remains in solution, the object of the present invention involving catalyst recovery and recycle without substantial decomposition and loss is achieved in an outstanding manner. As a result, the overall efficiency of the process is markedly increased. Similar achievement of the catalyst recovery and recycle object of the present invention when the latter (or alternative) isolation procedure is employed, is also feasible. Thus this object, which is particularly relevant when it is desired to effect the hydrogenolysis of the present process under continuous operating conditions, is achieved in an outstanding manner.

The following examples illustrate the present invention and the manner by which it can be practiced.

EXAMPLE 1

To a 300-milliliter Hastaloy C Magnedrive autoclave equipped with a mechanical stirrer was charged 10.0 grams (0.041 mole) of 4,4'-dihydroxyhydrobenzoin, 2.0 grams (0.0080 mole) of cobalt (II) acetate tetrahydrate, and 70 milliliters of 1-butanol. The reaction vessel was thereafter charged to 3300 pounds per square inch gauge (psig) with a mixture of hydrogen/carbon monoxide (2200 psig of hydrogen/1100 psig of carbon monoxide) and heated to 180° C with stirring at 800 revolutions per minute (rpm). The reaction was allowed to continue for a period of 1 hour. On cooling to about 50° C a homogeneous red liquid product solution was obtained. Gas chromatographic analysis of the solution showed the absence of any 4,4'-dihydroxyhydrobenzoin and that greater than 75 percent of the higher boiling components was 1,2-bis(4-hydroxyphenyl)ethane. Removal of the solvent (1-butanol) in vacuo followed by recrystallization of the resulting solid product from acetic acid gave an isolated yield of 6.2 grams (70.7 percent) of 1,2-bis(4-hydroxyphenyl)ethane as white crystals, melting point 199°–200° C. The identification of the product was confirmed by nuclear magnetic resonance spectroscopy and by gas chromatographic analysis of the volatile trimethylsilyl derivative, 1,2-bis(4-trimethylsilyloxyphenyl)ethane, which was prepared in accordance with conventional procedures by reaction of the white crystalline product with N,O-bis(-trimethylsilyl)trifluoroacetamide with pyridine as a catalyst at 130° C for about 5 minutes.

EXAMPLE 2

The procedure and reaction vessel (autoclave) described in EXAMPLE 1 above was employed with the exception that the autoclave was charged to 1100 psig with carbon monoxide and heated, with stirring at 800 rpm, to 200° C. Hydrogen was then charged to the autoclave to a total pressure of 3800 psig for a hydrogen to carbon monoxide molar ratio of 2:1. The reaction was allowed to continue for a period of 1 hour. After completion of the reaction, the reaction mixture and the autoclave were allowed to cool to about 70° C. The resulting product solution was placed in a flask and cooled overnight in a refrigerator (approximately 16 hours) at about 2° C to induce crystallization. The crystals were collected by suction filtration and recrystallized from acetic acid to yield 6.2 grams (71 percent) of 1,2-bis(4-hydroxyphenyl)ethane as white crystals.

The filtrate from the product solution, along with 10.0 grams (0.041 mole) of 4,4'-dihydroxyhydrobenzoin was charged to the autoclave and the reaction was repeated as described above three additional times for a total of four times. The yield from the four repetitive runs averaged about 71 percent.

EXAMPLE 3

To a 300-milliliter stainless steel Magnedrive autoclave equipped with a mechanical stirrer was charged 10.0 grams (0.041 mole) of 4,4'-dihydroxyhydrobenzoin, 1.7 grams (0.0050 mole) of cobalt octacarbonyl, and 70 milliliters of 1-butanol. The reactor was thereafter charged to 3300 psig with a mixture of hydrogen/carbon monoxide (2200 psig of hydrogen/1100 psig of carbon monoxide). The reaction was heated, with vigorous stirring, to 200° C, which temperature was maintained for a period of 1 hour. The reactor was cooled and gas chromatographic analysis of the resulting product solution showed the presence of 1,2-bis(4-hydroxyphenyl)ethane in 82 percent yield.

EXAMPLES 4–25

The procedure and reaction vessel described in EXAMPLE 2 above was employed for single batch operation, with the conditions, parameters and results as shown in TABLE 2.

TABLE 2

HYDROGENOLYSIS OF 4,4'-DIHYDROXYHYDROBENZOIN TO 1,2-BIS(4-HYDROXYPHENYL)ETHANE(BPE)[a]

| Ex. | Catalyst [Cobalt(II) Compound] | Catalyst Concentration (molar) | Concentration Ligand | Ligand Concentration (molar) | Reaction Temperature Solvent | Time (°C) | Pressure (hours) | Percentage Age (psig) | $H_2$[b] | Percentage Age Yield BPE |
|---|---|---|---|---|---|---|---|---|---|---|
| 4[c] | $Co(OCOCH_3)_2 \cdot 4H_2O$ | 0.11 | | | 1-Butanol | 220 | 1.0 | 3800 | 66 | 81.3 |
| 5 | $Co(OCOCH_3)_2 \cdot 4H_2O$ | 0.11 | | | 1-Butanol | 200 | 1.0 | 3800 | 66 | 74.6 |
| 6 | $Co(OCOCH_3)_2 \cdot 4H_2O$ | 0.11 | | | 1-Butanol | 200 | 1.0 | 3800 | 14 | 71.4 |
| 7 | $Co(OCOCH_3)_2 \cdot 4H_2O$ | 0.11 | | | 1-Butanol | 180 | 1.0 | 3800 | 66 | 66.4 |
| 8[d] | $Co(OCOCH_3)_2 \cdot 4H_2O$ | 0.11 | Pyridine | 0.26 | 1-Butanol | 180 | 1.0 | 3800 | 66 | 22.5 |
| 9[e] | $Co(OCOCH_3)_2 \cdot 4H_2O$ | 0.03 | $(C_4H_9)_3P$ | 0.06 | 1-Butanol | 180 | 21.0 | 3800 | 66 | 0.0 |
| 10 | $Co(OCOCH_3)_2 \cdot 4H_2O$ | 0.11 | | | 1-Butanol | 150 | 1.0 | 3800 | 66 | 53.2 |
| 11 | $Co(OCOCH_3)_2 \cdot 4H_2O$ | 0.11 | | | 1-Butanol | 150 | 3.0 | 3800 | 66 | 55.9 |
| 12 | $Co(OCOCH_3)_2 \cdot 4H_2O$ | 0.11 | | | 1-Butanol | 140 | 5.0 | 1000 | 50 | 58.6 |
| 13 | $Co(OCOCH_3)_2 \cdot 4H_2O$ | 0.11 | | | 1-Butanol | 130 | 5.0 | 1000 | 50 | 50.3 |
| 14 | $Co(OCOCH_3)_2 \cdot 4H_2O$ | 0.11 | | | 1-Butanol | 120 | 4.0 | 3800 | 66 | 44.3 |
| 15 | $Co(OCOCH_3)_2 \cdot 4H_2O$ | 0.11 | | | m-Cresol | 200 | 1.0 | 3800 | 66 | 0.0 |
| 16 | $Co(OCOCH_3)_2 \cdot 4H_2O$ | 0.11 | | | Ethanol | 200 | 1.0 | 3800 | 66 | 39.8 |
| 17 | $Co(OCOCH_3)_2 \cdot 4H_2O$ | 0.11 | | | 1-Hexanol | 180 | 1.0 | 3800 | 66 | 70.0 |
| 18 | $Co(OCOCH_3)_2 \cdot 4H_2O$ | 0.11 | | | Glycerine | 180 | 1.0 | 3800 | 66 | 0.0 |
| 19 | $Co(OCOCH_3)_2 \cdot 4H_2O$ | 0.11 | | | Nonanoic Acid | 200 | 1.0 | 3800 | 66 | 0.0 |
| 20 | $Co(OCOCH_3)_2 \cdot 4H_2O$ | 0.11 | | | Acetic Acid | 180 | 3.0 | 3800 | 66 | 10.2 |
| 21[h] | $Co_2(CO)_8$ | 0.09 | | | 1-Butanol | 200 | 1.0 | 3800 | 66 | 82.2 |
| 22 | $Co_2(CO)_8$ | 0.11 | | | 1-Butanol | 150 | 3.0 | 1000 | 50 | 52.7 |
| 23 | $Co_2(CO)_8$ | 0.11 | | | 1-Butanol | 140 | 3.0 | 1000 | 72 | 66.0 |
| 24 | $Co_2(CO)_8$ | 0.11 | | | 1-Butanol | 140 | 3.0 | 1000 | 66 | 57.8 |
| 25 | $Co_2(CO)_8$ | 0.11 | | | 1-Butanol | 140 | 3.0 | 1000 | 75 | 52.5 |

[a]All reactions had 70 milliliters of solvent and 10.0 grams (0.041 mole) of 4,4'-dihydroxyhydrobenzoin conducted in a 300-milliliter stirred autoclave.
[b]Balance of gas was carbon monoxide, CO.
[c]Cobalt(II) acetate tetrahydrate charged.
[d]Compound II is the major by-product.
[e]Compound II is the major by-product.
[f]No products were identifiable by gas chromatography.
[g]No products were identifiable by gas chromatography.
[h]Pre-formed dicobalt octacarbonyl charged.
[i]Cobalt metal plated out on autoclave wall due to insufficient CO partial pressure.

EXAMPLE 26

The autoclave described in EXAMPLE 1 was employed. To this autoclave was charged 11.0 grams (0.040 mole) of anisoin, 2.0 grams (0.0080 mole) of cobalt(II) acetate tetrahydrate, and 70 milliliters of 1-butanol. The autoclave was thereafter charged to 1100 psig with carbon monoxide and heated, with stirring at 800 rpm, to 200° C. Hydrogen was then charged to the autoclave to a total pressure of 3800 psig for a hydrogen to carbon monoxide molar ratio of 2:1. The reaction was allowed to continue for a period of 1 hour, and thereafter cooled to about 70° C. Gas chromatographic analysis of the homogeneous product solution indicated a 90 percent yield of 1,2-bis(4-methoxyphenyl)ethane.

EXAMPLE 27

The procedure and autoclave described in EXAMPLE 26 was employed with the exception that 10.0 grams (0.047 mole) of meso-hydrobenzoin was charged to the autoclave. Gas chromatographic analysis of the resulting product solution indicated a 23 percent yield of bibenzyl (1,2-diphenylethane), with the remainder of the product being desoxybenzoin.

The relatively low yield of bibenzyl was apparently due to insufficient reaction time to convert the intermediate, desoxybenzoin, to the final product, bibenzyl.

EXAMPLE 28

The procedure and autoclave described in EXAMPLE 26 was employed with the exception that 10.0 grams (0.047 mole) of dl-hydrobenzoin was charged to the autoclave. Gas chromatographic analysis of the resulting product solution indicated a 23 percent yield of bibenzyl (1,2-diphenylethane), with the remainder of the product being desoxybenzoin.

The relatively low yield of bibenzyl was apparently due to the same reasons as those set forth in EXAMPLE 27 above.

The 1,2-bis(aryl)ethane products produced in the present process have many and varied utilities due to the variety of functionalities contained therein. The 1,2-bis(hydroxyaryl)ethanes, for example, 1,2-bis(4-hydroxyphenyl)ethane, are useful as bactericides, chemical intermediates, monomer units for copolymers, and antioxidants. They are used to stabilize such materials as animal and vegetable fats or oils, gasoline, lubricants, polyalkenes such as polyethylene and polypropylene, and both natural and synthetic rubber. They are also used in the preparation of resins, for example, polyesters, polycarbonates, and the like resins, wherein they are used as the dihydroxy compound which is reacted either with phosgene, dibasic acids, dibasic acid halides, polyepoxides, polyurethanes, and the like.

Products containing other reactive functionalities, for example, the carboxy and/or cyano groups can also undergo condensation reactions in known manner to yield many useful polymeric materials, particularly polyesters. Moreover, the cyano functionality may be converted to other functionalities, for example, carboxy, ester, and the like, which as noted hereinabove, are useful in the formation of polyester polymeric materials.

Those products containing only less reactive functionalities are useful as chemical intermediates. For example, 1,2-diphenylethane (bibenzyl) is useful as an intermediate in at least one method of preparing styrene, a known article of commerce. Similarly, 1,2-bis(4-methylphenyl)ethane (p,p'-1,2-ditolylethane) can be directly oxidized to terephthalic acid or converted by known procedures to p-xylene which in turn can be oxidized to terephthalic acid. Terephthalic acid is an intermediate in the preparation of synthetic fibers of the glycol-terephthalic type, such fibers being known in the trade as Dacron, terylene, and the like.

Thus it is apparent that there has been provided, in accordance with the present invention, a process that fully satisfies the objects and advantages set forth hereinabove. While the invention has been described with respect to various specific examples and embodiments thereof, it will be understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the hydrogenolysis of hydrobenzoins which comprises
   (a) contacting the hydrobenzoin in an inert solvent system at hydrogenolysis conditions with a gaseous mixture of hydrogen and carbon monoxide and a homogeneous catalyst comprising cobalt carbonyl for a time sufficient to cause hydrogenolysis of the hydrobenzoin 1,2-diol functionality carbon-oxygen bonds wherein the oxygen so cleaved from each carbon atom is replaced by a hydrogen atom, and thereafter
   (b) recovering the product of such hydrogenolysis.

2. The process of claim 1 wherein the cobalt carbonyl is dicobalt octacarbonyl and/or cobalt hydrocarbonyl.

3. The process of claim 1 wherein the cobalt carbonyl is formed in situ from a cobalt(II) compound.

4. The process of claim 3 wherein the cobalt(II) compound is a cobalt(II) salt.

5. The process of claim 4 wherein the cobalt(II) salt is cobalt(II) acetate tetrahydrate.

6. The process of claim 1 wherein the hydrobenzoins are represented by the formula:

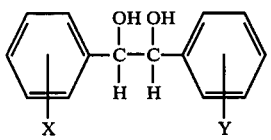

in which X and Y each independently represent hydrogen, alkyl of 1 to 8 carbon atoms, hydroxy, alkoxy containing an alkyl of 1 to 8 carbon atoms, acyloxy containing an alkyl of 1 to 8 carbon atoms or a phenyl, carboxy, cyano or halogen.

7. The process of claim 6 wherein the product of the hydrogenolysis of the hydrobenzoin is a 1,2-bis(aryl)ethane.

8. The process of claim 7 wherein the hydrobenzoin is 4,4'-dihydroxyhydrobenzoin and the hydrogenolysis product is 1,2-bis(4-hydroxyphenyl)ethane.

9. The process of claim 7 wherein the hydrobenzoin is 4,4'-dimethoxyhydrobenzoin and the hydrogenolysis product is 1,2-bis(4-methoxyphenyl)ethane.

10. The process of claim 7 wherein the hydrobenzoin is hydrobenzoin and the hydrogenolysis product is 1,2-diphenylethane.

11. The process of claim 7 wherein the hydrobenzoin is formed in situ from a benzoin under reaction conditions.

12. The process of claim 11 wherein the benzoin is 4,4'-dihydroxybenzoin.

13. The process of claim 11 wherein the benzoin is 4,4'-dimethoxybenzoin (anisoin).

14. The process of claim 11 wherein the benzoin is benzoin.

15. The process of claim 7 wherein the hydrobenzoin is formed in situ from a benzil under reaction conditions.

16. The process of claim 15 wherein the benzil is 4,4'-dihydroxybenzil.

17. The process of claim 15 wherein the benzil is 4,4'-dimethoxybenzil.

18. The process of claim 15 wherein the benzil is benzil.

19. The process of claim 1 wherein the hydrogenolysis conditions comprise temperatures between about 160° C and about 250° C and a total hydrogen and carbon monoxide pressure between about 1500 psig and about 10,000 psig.

20. The process of claim 19 wherein the molar ratio of hydrogen to carbon monoxide is between about 1:10 and about 5:1.

21. The process of claim 1 wherein the time sufficient to cause hydrogenolysis is between about 1 hour and about 5 hours.

22. The process of claim 1 wherein the inert solvent system comprises $C_2$ to $C_{10}$ aliphatic alcohols.

23. The process of claim 22 wherein the $C_2$ to $C_{10}$ aliphatic alcohol is a $C_4$ aliphatic alcohol.

24. The process of claim 23 wherein the $C_4$ aliphatic alcohol is 1-butanol.

25. The process of claim 1 wherein the catalyst comprising cobalt carbonyl is completely soluble in the inert solvent system.

26. The process of claim 25 wherein the concentration of the catalyst in the inert solvent system is within the range of about 0.05 molar to about 0.5 molar.

27. The process of claim 1 wherein the hydrobenzoin is soluble in the inert solvent system at least to the extent necessary to permit the hydrogenolysis to proceed at a reasonable rate.

28. The process of claim 1 wherein the reaction medium is acidic.

29. The process of claim 1 wherein the reaction medium contains no more than nominal amounts of water.

30. The process of claim 1 wherein the catalyst is recovered and reused in a subsequent hydrogenolysis of hydrobenzoins.

UNITED STATES PATENT OFFICE
CERTIFICATE OF CORRECTION

PATENT NO. : 4,087,463
DATED : May 2, 1978
INVENTOR(S) : Denis Forster and George F. Schaefer It is certified that error appears in the above-identified patent and that said Letters Patent are hereby corrected as shown below:

TABLE 2

Column 4, heading, delete "concentration."

Column 5, heading, delete "Temperature" and substitute therefor -- Concentration -- .

Column 6, heading, delete "Reaction Time."

Column 7, heading, delete "Pressure" and substitute therefor -- Temperature -- .

Column 8, heading, delete "Percentage" and substitute therefor -- Reaction Time -- .

Column 9, heading, delete "Percentage Yield" and substitute therefor -- Pressure -- .

Column 10, heading, above "$H_2^b$" insert -- Percentage -- .

Column 11, heading, above "BPE" insert -- Percentage Yield --

Example 25, Column 1, after numeral "25" add superscript -- i -- .

Signed and Sealed this

Nineteenth Day of September 1978

[SEAL]

Attest:

RUTH C. MASON
Attesting Officer

DONALD W. BANNER
Commissioner of Patents and Trademarks